United States Patent
Hestad

(10) Patent No.: US 9,468,475 B2
(45) Date of Patent: Oct. 18, 2016

(54) SPINAL STABILIZATION INSTALLATION INSTRUMENTATION AND METHODS

(71) Applicant: Zimmer Spine, Inc., Minneapolis, MN (US)

(72) Inventor: Hugh D. Hestad, Edina, MN (US)

(73) Assignee: Zimmer Spine, Inc., Edina, MN (US)

(*) Notice: Subject to any disclaimer, the term of this patent is extended or adjusted under 35 U.S.C. 154(b) by 0 days.

(21) Appl. No.: 14/332,873

(22) Filed: Jul. 16, 2014

(65) Prior Publication Data

US 2014/0330318 A1 Nov. 6, 2014

Related U.S. Application Data

(63) Continuation of application No. 13/872,446, filed on Apr. 29, 2013, now Pat. No. 8,821,550, which is a continuation of application No. 13/418,403, filed on Mar. 13, 2012, now Pat. No. 8,465,493, which is a continuation of application No. 12/334,031, filed on Dec. 12, 2008, now Pat. No. 8,137,355.

(51) Int. Cl.
*A61B 17/88* (2006.01)
*A61B 17/70* (2006.01)
(Continued)

(52) U.S. Cl.
CPC ....... *A61B 17/7083* (2013.01); *A61B 17/0642* (2013.01); *A61B 17/0682* (2013.01); *A61B 17/701* (2013.01); *A61B 17/7029* (2013.01); *A61B 17/7031* (2013.01);
(Continued)

(58) Field of Classification Search
CPC ..................... A61B 17/7053; A61B 2017/564
USPC .......... 606/246–279, 90, 329, 99, 103, 105, 606/86 A
See application file for complete search history.

(56) References Cited

U.S. PATENT DOCUMENTS

| 4,414,967 A | 11/1983 | Shapiro et al. |
| 4,454,875 A | 6/1984 | Pratt et al. |

(Continued)

FOREIGN PATENT DOCUMENTS

| EP | 516567 B1 | 7/1997 |
| EP | 0516567 B1 | 7/1997 |

(Continued)

OTHER PUBLICATIONS

Davis, Reginald J. et al., "Dynesys LIS Surgical Technique," Dynesys LIS Less Invasive Surgery, The Dynamic Stabilization System, 2005, Zimmer Spine, Inc., 24 pgs.
(Continued)

*Primary Examiner* — Ellen C Hammond
*Assistant Examiner* — Christina Negrellirodrigue
(74) *Attorney, Agent, or Firm* — Schwegman Lundberg & Woessner, P.A.

(57) ABSTRACT

A system for installing a vertebral stabilization system. The system includes an installation tool including a handle portion and a shaft extending distally from the handle portion. The shaft includes a conduit and a staple mechanism. The system also includes a flexible implant member extending along the conduit configured to be advanced out from a distal end of the shaft, and a staple housed in the staple mechanism. The staple is configured to secure the flexible implant member to a vertebra. The handle portion is configured to selectively advance the flexible implant member from the shaft and to selectively actuate the staple mechanism.

20 Claims, 15 Drawing Sheets

(51) Int. Cl.
*A61B 17/064* (2006.01)
*A61B 17/068* (2006.01)
*A61B 17/10* (2006.01)

(52) U.S. Cl.
CPC ........ *A61B 17/7076* (2013.01); *A61B 17/105* (2013.01); *A61B 2017/0641* (2013.01); *A61B 2017/0647* (2013.01)

(56) References Cited

U.S. PATENT DOCUMENTS

| | | | |
|---|---|---|---|
| 4,500,025 A | 2/1985 | Skwor | |
| 4,527,726 A | 7/1985 | Assell et al. | |
| 4,570,623 A | 2/1986 | Ellison et al. | |
| 5,352,229 A | 10/1994 | Goble et al. | |
| 5,575,054 A | 11/1996 | Klinzing et al. | |
| 5,720,753 A | 2/1998 | Sander et al. | |
| 6,146,406 A | 11/2000 | Shluzas et al. | |
| 6,616,669 B2 | 9/2003 | Ogilvie et al. | |
| 8,137,355 B2 | 3/2012 | Hestad | |
| 8,465,493 B2 | 6/2013 | Hestad | |
| 8,821,550 B2 | 9/2014 | Hestad | |
| 9,277,940 B2* | 3/2016 | Rice ................... | A61B 17/7031 |
| 2004/0133201 A1 | 7/2004 | Shluzas et al. | |
| 2007/0005063 A1 | 1/2007 | Bruneau et al. | |
| 2007/0078461 A1 | 4/2007 | Shluzas | |
| 2007/0100341 A1 | 5/2007 | Reglos et al. | |
| 2007/0118119 A1 | 5/2007 | Hestad | |
| 2007/0129729 A1 | 6/2007 | Petit | |
| 2007/0156245 A1 | 7/2007 | Cauthen et al. | |
| 2007/0198088 A1 | 8/2007 | Biedermann et al. | |
| 2007/0225710 A1 | 9/2007 | Jahng et al. | |
| 2007/0233075 A1 | 10/2007 | Dawson | |
| 2007/0233087 A1 | 10/2007 | Schlapfer | |
| 2007/0233095 A1 | 10/2007 | Schlaepfer | |
| 2007/0239158 A1 | 10/2007 | Trieu et al. | |
| 2007/0270821 A1 | 11/2007 | Trieu et al. | |
| 2007/0270860 A1 | 11/2007 | Jackson | |
| 2007/0293862 A1 | 12/2007 | Jackson | |
| 2008/0009792 A1 | 1/2008 | Henniges et al. | |
| 2008/0009863 A1* | 1/2008 | Bond ................... | A61B 17/025 606/86 A |
| 2008/0021459 A1 | 1/2008 | Lim | |
| 2008/0021465 A1 | 1/2008 | Shadduck et al. | |
| 2008/0039843 A1 | 2/2008 | Abdou | |
| 2008/0091213 A1 | 4/2008 | Jackson | |
| 2008/0140076 A1 | 6/2008 | Jackson | |
| 2008/0140133 A1* | 6/2008 | Allard ................. | A61B 17/705 606/308 |
| 2008/0147122 A1 | 6/2008 | Jackson | |
| 2008/0161857 A1 | 7/2008 | Hestad et al. | |
| 2008/0177317 A1 | 7/2008 | Jackson | |
| 2008/0183216 A1 | 7/2008 | Jackson | |
| 2008/0195153 A1 | 8/2008 | Thompson | |
| 2008/0234737 A1 | 9/2008 | Boschert | |
| 2008/0234738 A1* | 9/2008 | Zylber et al. ......... | 606/254 |
| 2008/0234744 A1 | 9/2008 | Zylber et al. | |
| 2008/0249531 A1* | 10/2008 | Patterson ............. | A61B 34/76 606/99 |
| 2008/0262551 A1 | 10/2008 | Rice et al. | |
| 2008/0275456 A1 | 11/2008 | Vonwiller et al. | |
| 2008/0294198 A1 | 11/2008 | Jackson | |
| 2008/0300633 A1 | 12/2008 | Jackson | |
| 2008/0319486 A1 | 12/2008 | Hestad et al. | |
| 2009/0005817 A1 | 1/2009 | Friedrich et al. | |
| 2009/0012562 A1 | 1/2009 | Hestad et al. | |
| 2009/0030420 A1 | 1/2009 | Runco et al. | |
| 2009/0036924 A1 | 2/2009 | Egli et al. | |
| 2009/0082815 A1 | 3/2009 | Zylber et al. | |
| 2009/0093846 A1 | 4/2009 | Hestad | |
| 2009/0099606 A1 | 4/2009 | Hestad et al. | |

FOREIGN PATENT DOCUMENTS

| | | |
|---|---|---|
| EP | 0669109 B1 | 5/1999 |
| EP | 669109 B1 | 5/1999 |
| EP | 1719468 A1 | 11/2006 |
| EP | 1523949 B1 | 6/2007 |
| EP | 1523949 B1 | 6/2007 |
| FR | 2715057 B1 | 3/1996 |
| FR | 2775583 B1 | 8/2000 |
| FR | 2844180 B1 | 8/2005 |
| FR | 2867057 B1 | 6/2007 |
| NL | 7610576 A | 3/1978 |
| WO | 9519149 A1 | 7/1995 |
| WO | 9905980 A1 | 2/1999 |
| WO | 9944527 A1 | 9/1999 |
| WO | 2004024011 A1 | 3/2004 |
| WO | 2004089244 A3 | 10/2004 |
| WO | 2005037150 A1 | 4/2005 |
| WO | 2005037110 A3 | 8/2005 |
| WO | 2005087121 A1 | 9/2005 |
| WO | 2006066685 A1 | 6/2006 |
| WO | 2007087476 A1 | 8/2007 |
| WO | 2007044795 A3 | 10/2007 |
| WO | 2008034130 A2 | 3/2008 |
| WO | 2008006098 B1 | 4/2008 |
| WO | 2008013892 A3 | 6/2008 |
| WO | 2008021319 A3 | 8/2008 |
| WO | 2008034130 A3 | 10/2008 |
| WO | 2008134703 A2 | 11/2008 |
| WO | 2008134703 A3 | 1/2009 |

OTHER PUBLICATIONS

Foster-Miller "Tools for Minimally Invasive Surgery" [online]. Retrieved from the Internet: http://www.foster-miller.com/projectexamples/medical_devices/tools_for_minimally_invasi . . . [retrieved on Jan. 8, 2009] 1 pg.

"U.S. Appl. No. 12/334,031, Final Office Action mailed Aug. 3, 2011", 7 pgs.

"U.S. Appl. No. 12/334,031, Non Final Office Action mailed Feb. 17, 2011", 7 pgs.

"U.S. Appl. No. 12/334,031, Notice of Allowance mailed Nov. 14, 2011", 5 pgs.

"U.S. Appl. No. 12/334,031, Response filed May 16, 2011 to Non Final Office Action mailed Feb. 17, 2011", 11 pgs.

"U.S. Appl. No. 12/334,031, Response filed Sep. 30, 2011 to Final Office Action mailed Aug. 3, 2011", 6 pgs.

"U.S. Appl. No. 13/418,403, Final Office Action mailed Dec. 19, 2012", 10 pgs.

"U.S. Appl. No. 13/418,403, Non Final Office Action mailed Jun. 29, 2012", 8 pgs.

"U.S. Appl. No. 13/418,403, Notice of Allowance mailed Feb. 25, 2013", 5 pgs.

"U.S. Appl. No. 13/418,403, Response filed Feb. 12, 2013 to Final Office Action mailed Dec. 19, 2012", 5 pgs.

"U.S. Appl. No. 13/418,403, Response filed Sep. 25, 2012 to Non Final Office Action mailed Jun. 29, 2012", 9 pgs.

"U.S. Appl. No. 13/872,446, Non Final Office Action mailed Dec. 2, 2013", 7 pgs.

"U.S. Appl. No. 13/872,446, Notice of Allowance mailed May 15, 2014", 9 pgs.

"U.S. Appl. No. 13/872,446, Response filed Jan. 21, 2014 to Non Final Office Action mailed Dec. 2, 2013", 9 pgs.

* cited by examiner

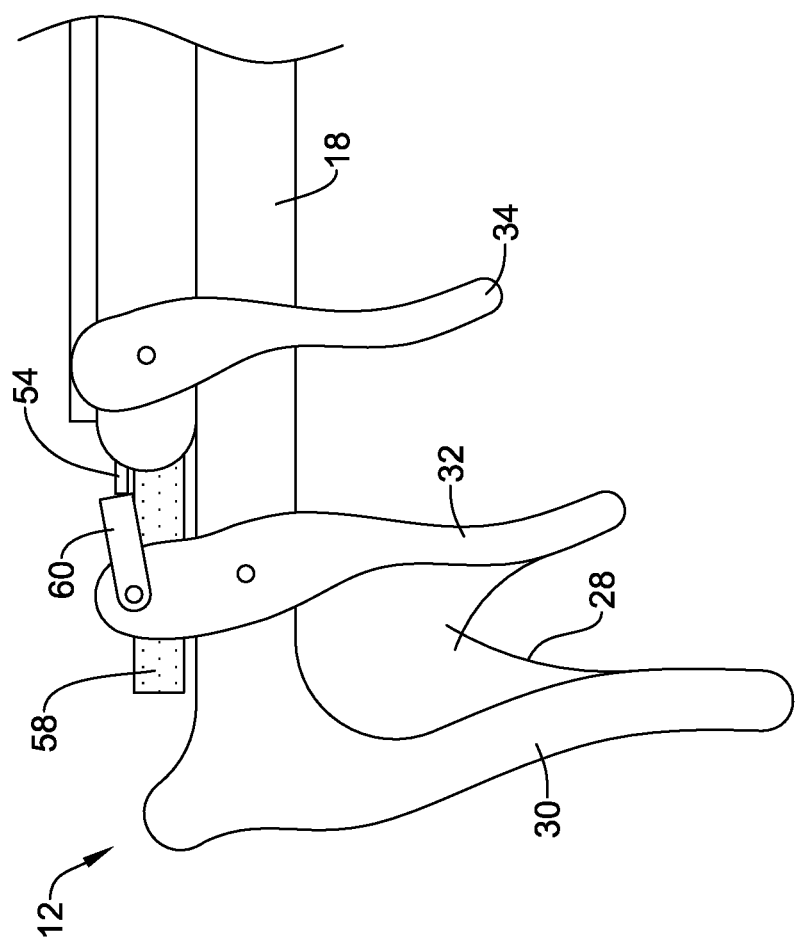

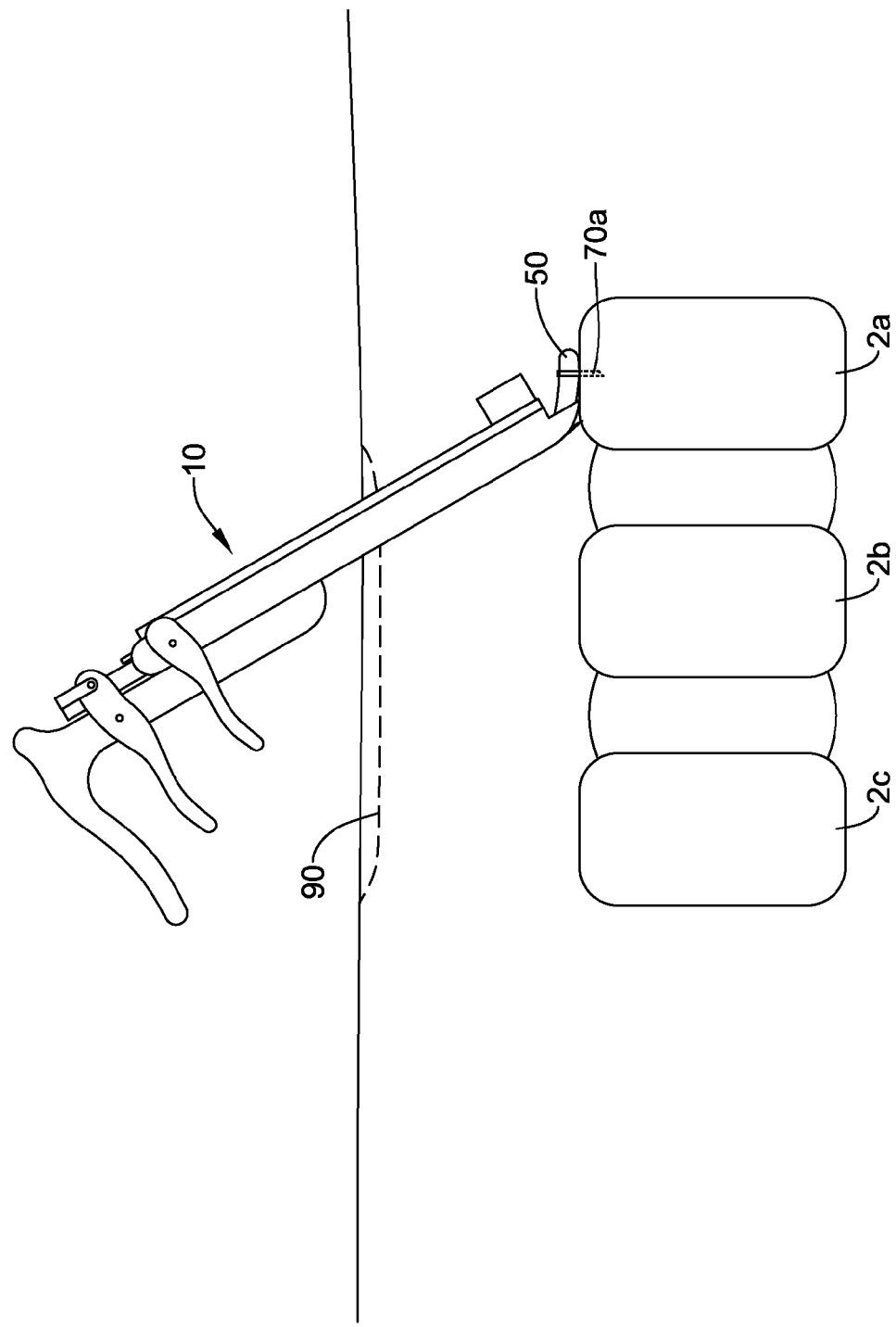

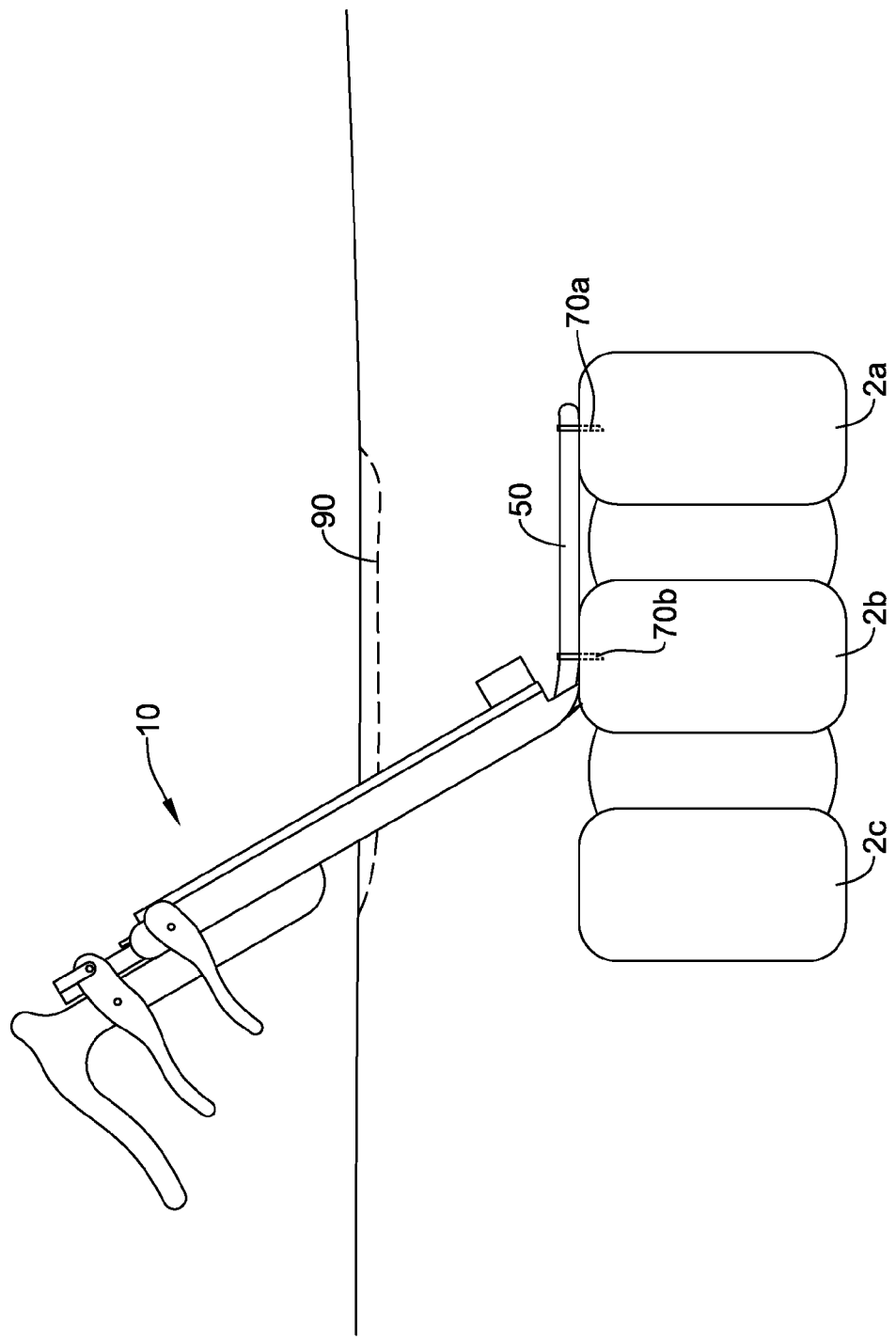

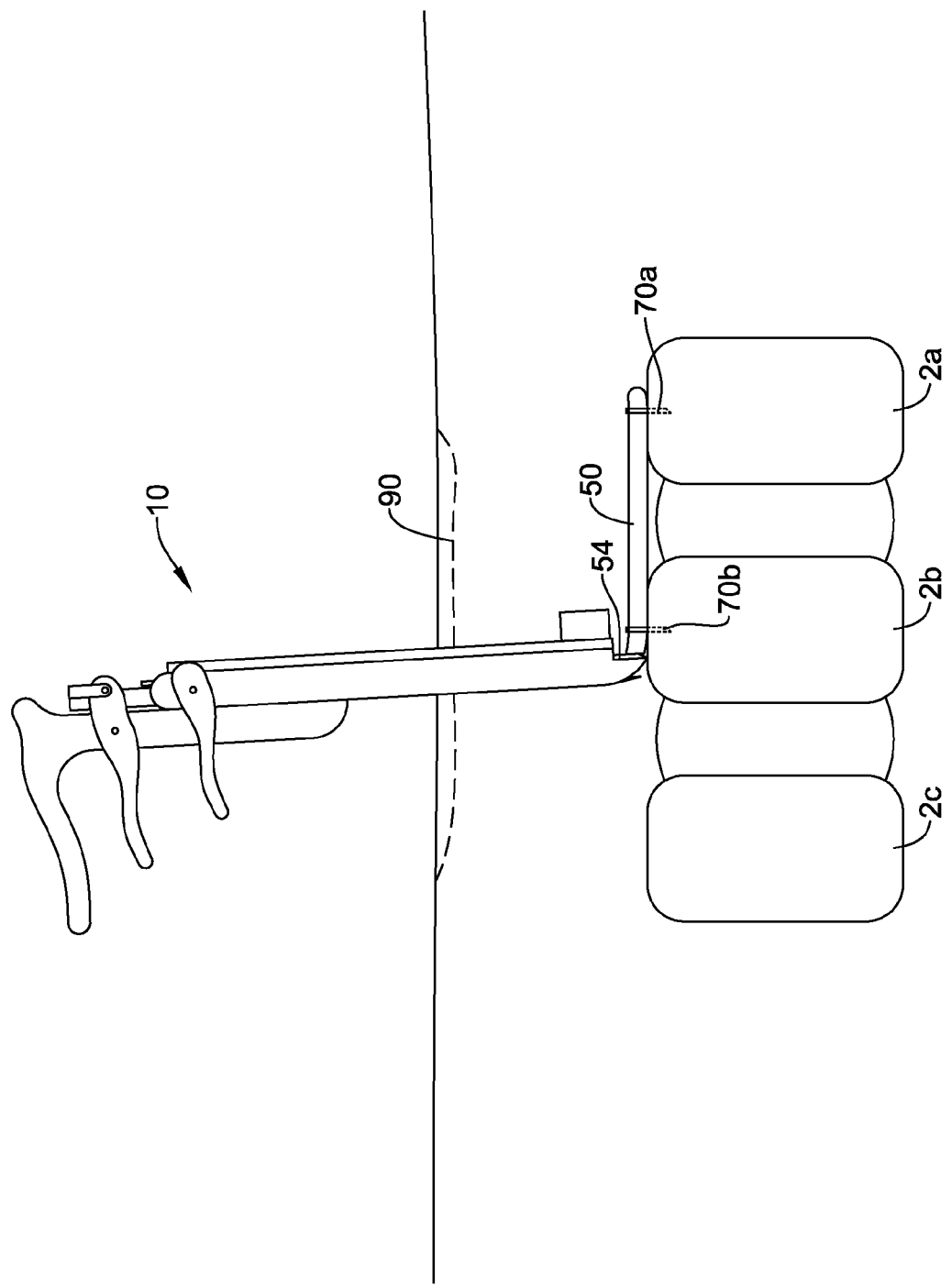

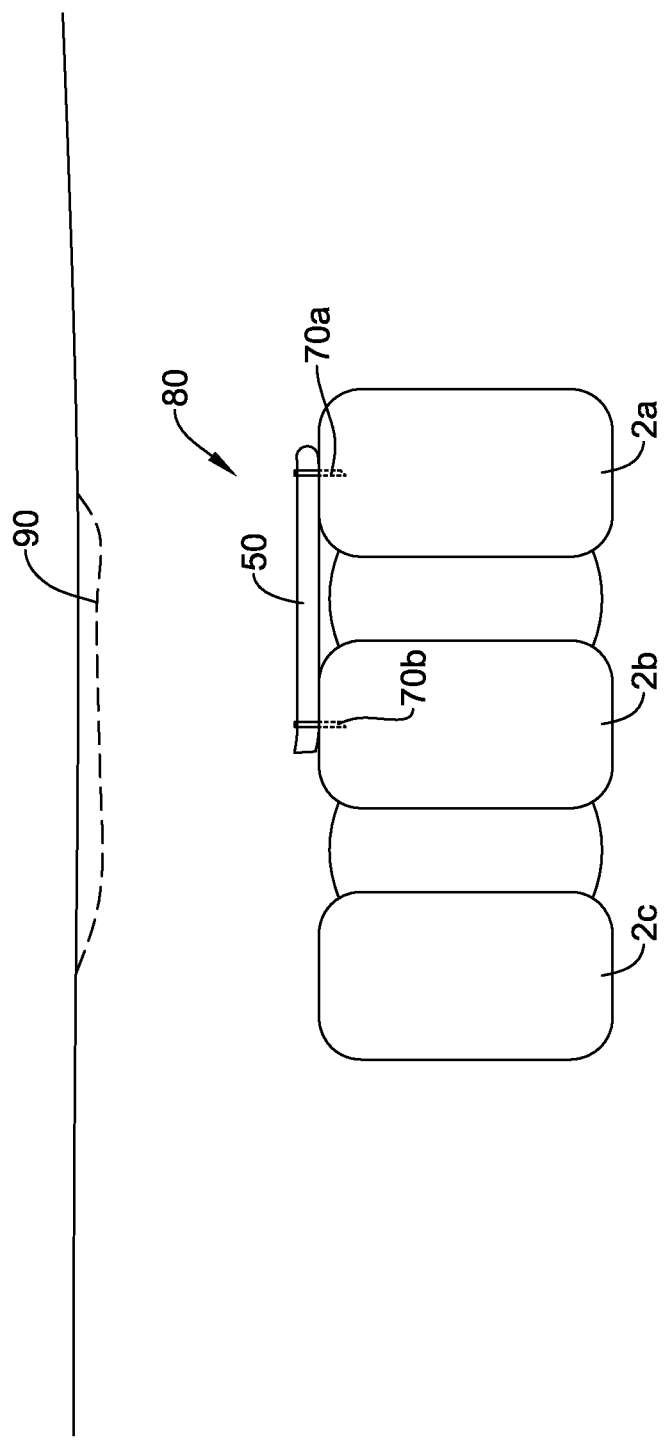

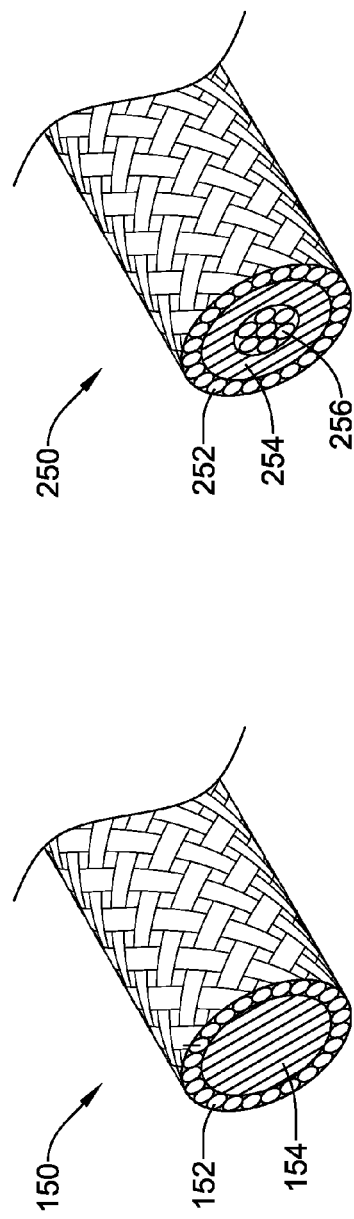
Figure 11B
Figure 11A
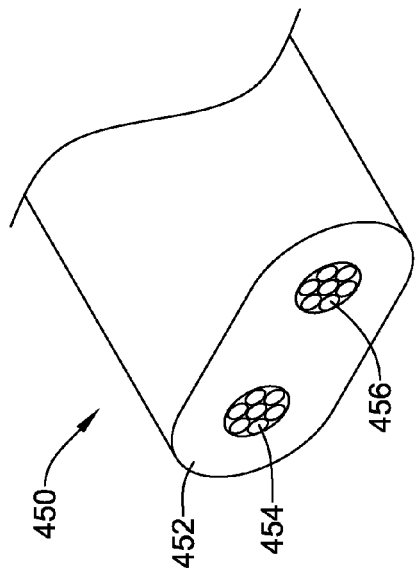
Figure 11D
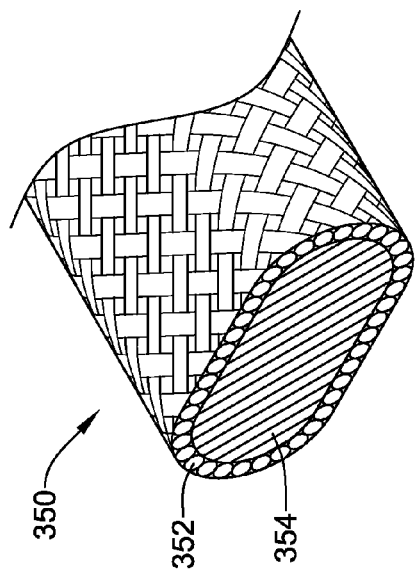
Figure 11C

SPINAL STABILIZATION INSTALLATION INSTRUMENTATION AND METHODS

CROSS-REFERENCE TO RELATED APPLICATIONS

This application is a continuation of U.S. patent application Ser. No. 13/872,446, filed on Apr. 29, 2013, which is a continuation of U.S. patent application Ser. No. 13/418,403, filed on Mar. 13, 2012, now U.S. Pat. No. 8,465,493, which is a continuation of U.S. patent application Ser. No. 12/334,031, filed on Dec. 12, 2008, now U.S. Pat. No. 8,137,355, the entire disclosures of which are incorporated herein by reference.

TECHNICAL FIELD

The disclosure is directed to installation instrumentation and methods of installing a spinal stabilization system on a region of a spinal column. More particularly, the disclosure is directed to an installation tool and method for advancing an elongate flexible stabilization member between adjacent vertebrae and anchoring the stabilization member to the adjacent vertebrae of a spinal column.

BACKGROUND

The spinal column of a patient includes a plurality of vertebrae linked to one another by facet joints and an intervertebral disc located between adjacent vertebrae. The facet joints and intervertebral disc allow one vertebra to move relative to an adjacent vertebra, providing the spinal column a range of motion. Diseased, degenerated, damaged, or otherwise impaired facet joints and/or intervertebral discs may cause the patient to experience pain or discomfort and/or loss of motion, thus prompting surgery to alleviate the pain and/or restore motion of the spinal column.

Methods of treating spinal column disorders include installing a spinal stabilization system to stabilize a segment of the spinal column. One conventional spinal stabilization system includes securing a rigid rod between two or more vertebrae with pedicle screws. Another technique utilizes a less rigid connecting element to provide a more dynamic stabilization of the affected segment of the spinal column. One example of a dynamic stabilization system is the DYNESYS system available from Zimmer Spine, Inc. of Minneapolis, Minn. Such dynamic stabilization systems may include a flexible, tubular spacer positioned between pedicle screws installed between adjacent vertebrae. The spacer is positioned between the pedicle screws and a flexible cord is threaded through the spacer. The flexible cord is secured to the heads of the pedicle screws by set screws, thereby retaining the spacer between the pedicle screws while cooperating with the spacer to permit mobility of the spine.

Some such surgical techniques may be found quite invasive and time consuming. Thus, it is desirable to achieve dynamic stabilization of a spinal segment in a less invasive and/or less time consuming manner. Therefore, alternative systems and associated methods for installing a vertebral stabilization system are desirable.

SUMMARY

The disclosure is directed to several alternative designs, materials and methods of manufacturing medical device structures and assemblies.

Accordingly, one illustrative embodiment is an installation tool for installing a vertebral stabilization system. The installation tool includes a handle portion and an elongate shaft extending distally from the handle portion. The elongate shaft of the installation tool includes a conduit for directing a flexible implant member to a vertebra of a spinal column and an anchoring mechanism for applying an anchor to the vertebra to secure the flexible implant member to the vertebra.

Another illustrative embodiment is a system for installing a vertebral stabilization system. The system includes an installation tool including a handle portion and a shaft extending distally from the handle portion. The shaft includes a conduit and a staple mechanism. The system also includes a flexible implant member extending along the conduit configured to be advanced out from a distal end of the shaft, and a staple housed in the staple mechanism. The staple is configured to secure the flexible implant member to a vertebra. The handle portion is configured to selectively advance the flexible implant member from the shaft and to selectively actuate the staple mechanism.

Yet another illustrative embodiment is a medical procedure for installing a vertebral stabilization system. During the procedure an installation tool is inserted through an incision of a patient to a first vertebra of a spinal column. The installation tool includes a handle portion and a shaft extending from the handle portion. The shaft of the installation tool includes a conduit for directing a flexible implant member and an anchoring mechanism for applying an anchor. A flexible implant member is advanced along the conduit and out from a distal end of the shaft of the installation tool. The anchoring mechanism is actuated to expel a first anchor to secure the flexible implant member to the first vertebra.

With the flexible implant member secured to the first vertebra, the flexible implant member is further advanced along the conduit and out from the distal end of the shaft of the installation tool while moving the distal end of the shaft to a second vertebra. The anchoring mechanism is actuated to expel a second anchor to secure the flexible implant member to the second vertebra. An excess portion of the flexible implant member may then be cut away.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 3 is an enlarged view of the proximal portion of the installation tool of FIG. 1 with the switching member switched to a second position;

FIGS. 4A-4E illustrate an exemplary method of installing a vertebral stabilization system with the installation tool of FIG. 1;

FIGS. 11A-11D illustrate various exemplary embodiments of an elongate flexible member of a vertebral stabilization system.

Figure 1:
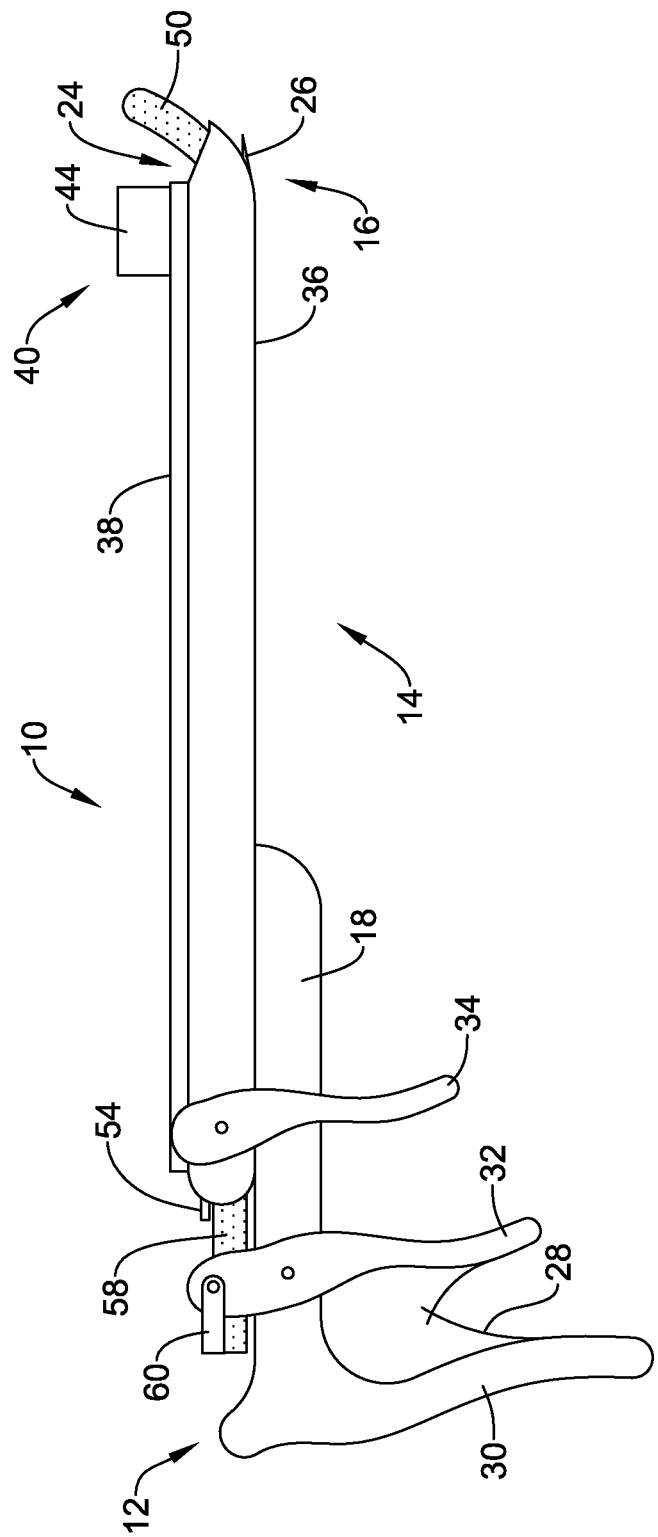
FIG. 1 is a side view of an exemplary installation tool for installing a vertebral stabilization system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The use of the term "stabilization" in the present description refers to securing adjacent vertebrae such that the movement between the adjacent vertebrae is limited to a desired amount. Stabilization may also be achieved by not only reducing movement, but also by simply providing increased structural integrity between adjacent vertebrae.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to FIG. 1, there is shown an installation tool 10 configured for delivering and installing a spinal stabilization system such as a dynamic stabilization system to a spinal segment. In some circumstances, the installation tool 10 may be utilized to implant a spinal stabilization system to a vertebral segment in a percutaneous or minimally invasive manner.

The installation tool 10 may include a handle portion 12 and an elongate shaft 14 extending distally from the handle portion 12. In some embodiments, the elongate shaft 14 may extend axially along a longitudinal axis of the installation tool 10, while in other embodiments the elongate shaft 14, or portions thereof, may be offset or otherwise deviate from the longitudinal axis of the installation tool 10.

The installation tool 10 may be configured to perform one or more, or a plurality of actions in installing a vertebral stabilization system on a vertebral segment of a spinal column. For instance, the installation tool 10 may advance an elongate flexible stabilization member 50 from the distal end 16 of the shaft 14 of the installation tool 10, may secure one or more, or a plurality of anchors to secure the elongate flexible stabilization member 50 to vertebrae of the spinal column, may distract adjacent vertebrae, and/or may cut away excess portions of the elongate flexible stabilization member 50.

Figure 2:
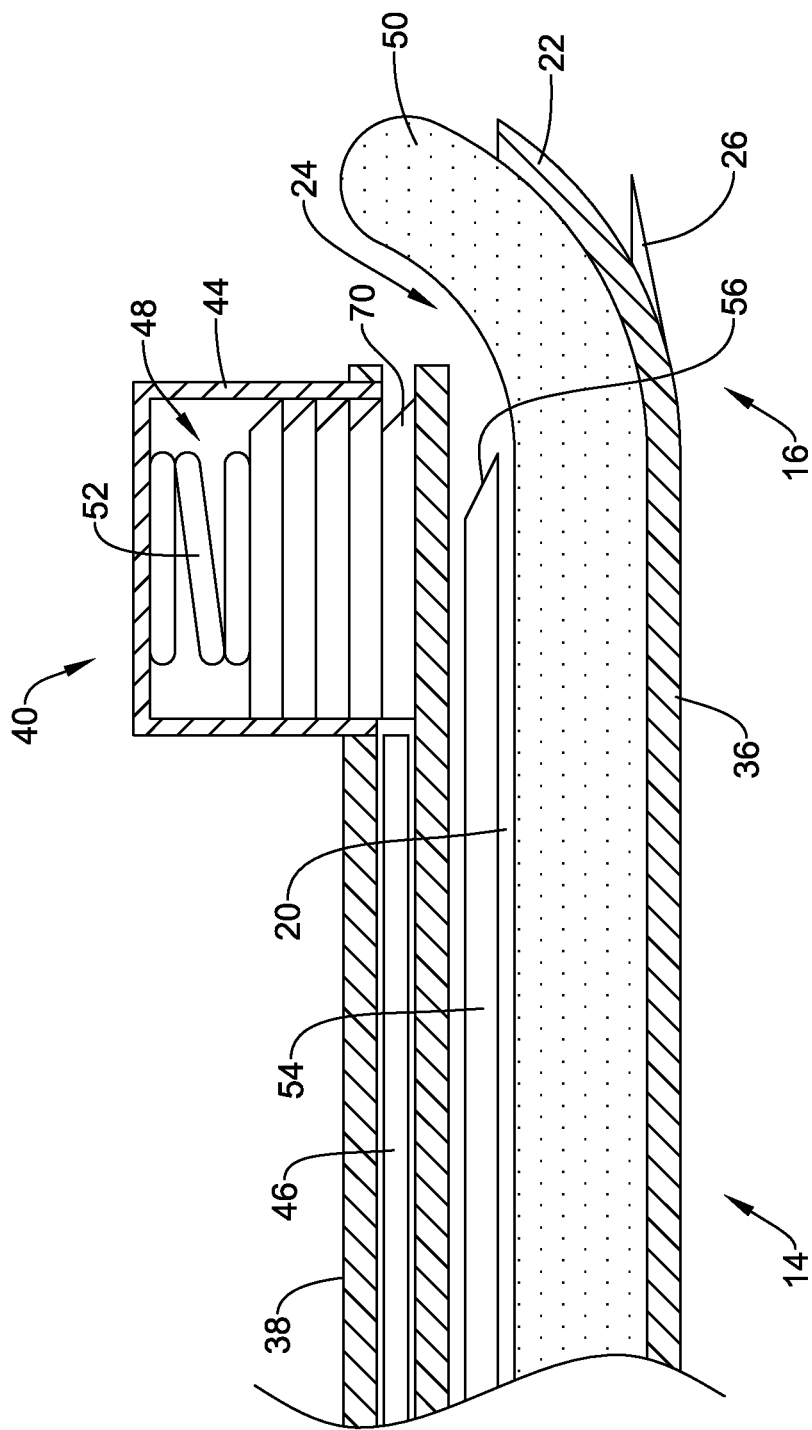
FIG. 2 is an enlarged view of the distal portion of the installation tool of FIG. 1.

As further shown in FIG. 2, the installation tool 10 may include a conduit 20, such as an enclosed, partially enclosed, or open conduit. As shown in FIG. 2, the conduit 20 may be defined, at least in part, by a first tubular member 36 of the elongate shaft 14. The conduit 20 may be configured to hold and direct a flexible stabilization member 50 from the distal end 16 of the installation tool 10. For instance, as shown in FIGS. 1 and 2, the conduit 20, through which the flexible stabilization member 50 extends through, may extend from a proximal portion of the shaft 14 to the distal end 16 of the shaft 14 along a longitudinal axis of the elongate shaft 14.

The elongate shaft 14 may include a ramp 22 proximate the distal end 16 of the shaft 14 configured to redirect the directional movement of the stabilization member 50 upon exiting the distal opening 24 of the shaft 14. For example, the ramp 22 may be an arcuate or sloped ramp extending non-parallel to the longitudinal axis of the shaft 14. Furthermore, in some embodiments the distal opening 24 may lie in a plane which is not perpendicular to the longitudinal axis of the shaft 14. In such an embodiment, the stabilization member 50 may be translated distally along the longitudinal axis of the shaft 14 until the stabilization member 50 reaches the ramp 22, at which point, the ramp 22 redirects the stabilization member 50 out the distal opening 24 in a direction which is not parallel with the longitudinal axis of the shaft 14.

Additionally or alternatively to a ramp 22, the stabilization member 50 may be precurved such that as the stabilization member 50 exits the distal opening 24 of the installation tool 10 the stabilization member 50 attempts to revert to the precurved configuration. For instance, the stabilization member 50 may be held in a substantially straight configuration in the conduit 20 of the shaft 14, but may assume the curved configuration when not constrained by the conduit 20. Thus, as the stabilization member 50 exits the distal opening 24 the stabilization member 50 extends in a direction which is not parallel with the longitudinal axis of the shaft 14. This may help position the stabilization member 50 along the vertebrae as the stabilization member 50 exits the shaft 14 of the installation tool 10.

In some embodiments, the installation tool 10 may include one or more structural features used in distracting adjacent vertebrae. For example, the installation tool 10 may include one or more, or a plurality of prongs 26 extending from the distal end 16 of the elongate shaft 14. The prong 26 may be configured to project or bite into a vertebrae during a medical procedure, such that medical personnel may use the installation tool 10 to distract the vertebra from an adjacent vertebra during the medical procedure.

The installation tool 10 may also include an anchoring mechanism 40, which is actuatable to expel an anchor 70 from the distal end 16 of the installation tool 10 to anchor the stabilization member 50 to a vertebra. For instance, in some embodiments the anchoring mechanism 40 may be a stapling mechanism configured to expel a staple from the distal end 16 of the installation tool 10.

The anchoring mechanism 40 may be preloaded with one or more, or a plurality of anchors 70 prior to the medical procedure. In some embodiments, the anchoring mechanism 40 may include a cartridge 44, such as a removable cartridge, which may house a plurality of anchors 70 for use during a medical procedure. The cartridge 44 may feed the plurality of anchors 70, one at a time, to a driver 46 which is actuatable to expel the anchor 70 from the installation tool 10 and drive the anchor 70 into the vertebra. In some embodiments, the driver 46 may be mechanically actuated, pneumatically actuated, spring actuated, or otherwise actuated to expel an anchor 70 from the installation tool 10. In some embodiments, such as shown in FIG. 3, the driver 46 may extend along a second tubular member 38 of the shaft 14 of the installation tool 10.

The cartridge 44 may include a feeding mechanism 48, which in some instances, may include a spring member 52 configured to deliver the anchors 70 to and/or align the anchors 70 with the driver 46 to effectuate expelling the anchor 70 from the distal end 16 of the installation tool 10.

In some embodiments, the cartridge 44 may be loaded with a plurality of anchors 70 and then removably coupled to the elongate shaft 14 of the installation tool 10 prior to the medical procedure. Thus, the installation tool 10 may be reused in a subsequent procedure by replacing and/or refilling the cartridge 44. In some embodiments, the installation tool 10 may be preloaded with a sufficient quantity of anchors 70 to complete installation of the stabilization member 50 without withdrawing the shaft 14 of the installation tool 10 from the patient until the installation is completed. For instance, the cartridge 44 may be preloaded with two, three, four, six, eight or more anchors 70 prior to performing the medical procedure. In other embodiments, an anchor 70 may be fed to the anchoring mechanism 40 by the medical personnel on demand as necessary.

In some embodiments, the installation tool 10 may be configured such that medical personnel may manually load an anchor 70 in the installation tool 10 from the proximal end of the installation tool 10 during the medical procedure. The medical personnel may then manually install the anchor 70 into a vertebra as desired. For instance, in some embodiments an anchor 70 may be disposed in a channel formed by the second tubular member 38, or other channel of the installation tool 10 extending from a proximal portion of the shaft 14 remaining external of the patient's body to the distal end 16 of the shaft 14. The channel may be used to deliver the anchor 70 to the distal end 16 of the shaft 14 in order to be driven into the vertebra. The medical personnel may then manually use a tamping device or other driver, to drive the anchor 70 into the bone. Additional anchors 70 may be loaded in the channel and individually driven into a bone by medical personnel during the medical procedure, as needed.

In some embodiments, the installation tool 10 may include a cutter 54 which may be used to cut away an excess portion of the stabilization member 50 during a medical procedure. The cutter 54 may extend along the shaft 14 of the installation tool 10. In some instances, the cutter 54 may have a sharpened tip 56 which may be selectively brought into contact with the stabilization member 50 to sever a portion of the stabilization member 50 extending out of the installation tool 10 from a portion of the stabilization member 50 remaining in the conduit 20 of the installation tool 10. In other instances, the cutter 54 may include a plurality of jaws which may be actuated toward one another to sever the stabilization member 50 positioned between the jaws of the cutter 54. It is noted that other cutting means may be utilized with the installation tool 10, including a separate cutting tool, to cut away excess portions of the stabilization member 50, if desired.

The handle portion 12 of the installation tool 10 may be used to manipulate the installation tool 10 and/or to actuate one or more components of the installation tool 10 during the medical procedure. As shown in FIG. 1, the handle portion 12 may include a palm grip 30 rigidly mounted to a base portion 18 of the shaft 14 of the installation tool 10. The palm grip 30 may be ergonomically formed to fit comfortably in the palm of the hand of medical personnel using the installation tool 10.

The handle portion 12 may also include a first trigger or actuatable handle 32 which may be used to selectively control one or more of the operative features of the installation tool 10. For instance, the first actuatable handle 32 may be configured to advance the stabilization member 50 from the distal end 16 of the installation tool 10 when the actuatable handle 32 is actuated. For instance, the first handle 32 may engage with a proximal portion or extension 58 the stabilization member 50 to urge the stabilization member 50 distally.

The first actuatable handle 32 may be pivotably mounted to the shaft 14 such that the first actuatable handle 32 may be actuated relative to the palm grip 30. Actuation of the first actuatable handle 32 may urge to stabilization member 50 distally along the conduit 20 to advance the stabilization member 50 from the distal opening 24. The handle portion 12 may include a spring 28 or other biasing means biasing the first actuatable handle 32 away from the palm grip 30. Thus, advancement of the stabilization member 50 may be performed by actuating the first handle 32 toward the palm grip 30. In some embodiments, a single stroke of the first handle 32 may advance the stabilization member 50 from the installation tool 10 a sufficient distance. In other embodiments, a series of strokes of the first handle 32 toward the palm grip 30 may be performed, in which the stabilization member 50 moves more distally from the installation tool 10 during each of the series of strokes.

The handle portion 12 may include a second trigger or actuatable handle 34 which may be used to selectively control one or more of the operative features of the installation tool 10. For instance, the second actuatable handle 34 may be configured to actuate the driver 46 to expel an anchor 70 from the installation tool 10 when the second handle 34 is actuated. For instance, the second handle 34 may operate and/or release, a lever, valve, cam, rod, spring, or other mechanism of the anchoring mechanism 40 to expel an anchor 70 from the installation tool 10.

The second actuatable handle 34 may be pivotably mounted to the shaft 14 such that the second actuatable handle 34 may be actuated relative to the palm grip 30. Actuation of the second actuatable handle 34 may initiate activation of the driver 46 to expel an anchor 70 from the installation tool 10. For instance, the second actuatable handle 34 may be moved toward the palm grip 30 in order to expel an anchor 70 from the installation tool 10. Thus, an anchor 70 may be discharged from the installation tool 10 with each stroke of the second handle 34 in some instances.

Additionally, one of the first and/or second actuatable handles 32, 34 may be selectively used to selectively control the cutter 54, or the installation tool 10 may include a third trigger or actuatable handle to control the cutter 54. For instance, as shown in FIGS. 1 and 3, the first actuatable handle 32 may selectively control actuation of the cutter 54.

The installation tool 10 may include a control mechanism 60, such as a button, switch, toggle, clip, lever, or other feature, which may be manipulated to selectively control operation of the first actuatable handle 32. For instance, when the control mechanism 60 is in a first position, shown in FIG. 1, actuation of the first handle 32 may advance the stabilization member 50 from the installation tool 10. When the control mechanism 60 is moved to a second position, shown in FIG. 3, actuation of the first handle 32 may actuate the cutter 54 to sever the stabilization member 50 as discussed above. For instance, in the second position shown in FIG. 3, actuation of the first handle 32 may force the control mechanism 60 against a proximal portion of the cutter 54, urging the cutter 54 distally to cut the stabilization member 50. However, in the first position shown in FIG. 1, actuation of the first handle 32 may not result in actuation of the cutter 54.

It is noted that in some embodiments, the second actuatable handle 32, or an additional handle, may include a control mechanism which may selectively control actuation of a plurality of operative features of the installation tool 10.

FIGS. 4A-4E illustrate an exemplary method of installing a vertebral stabilization system 80 with the installation tool 10 during a medical procedure. In some embodiments, the spinal column of a patient may be accessed in a percutaneous or minimally invasive manner by passing the shaft 14 of the installation tool 10 through an incision 90. In some embodiments, an access cannula, retractor, or other device (not shown) may be inserted into the incision 90 to maintain access to adjacent vertebrae 2a, 2b during the medical procedure. In other embodiments, access to the adjacent vertebrae 2a, 2b may be maintained directly through the incision 90. The vertebrae 2a, 2b may be accessed through a posterior approach, an anterior approach, a lateral approach, a translateral approach, a posterio-lateral approach, or other desired approach.

Having gained access to the adjacent vertebrae 2a, 2b of the spinal column, the distal end 16 of the installation instrument 10 may be moved adjacent to the first vertebra 2a and a portion of the stabilization member 50 may be advanced out of the distal end 16 of the installation instrument 10. For instance, the first handle 32 may be actuated to move the stabilization member 50 distally out of the distal opening 24 of the installation tool 10. The ramp 22 may redirect the exposed portion of the stabilization member 50 in a direction generally parallel to the spinal column, while the elongate shaft 14 is positioned at an angle, such as an acute angle, to the spinal column.

With the stabilization member 50 positioned at a desired location on the first vertebra 2a, such as the pedicle, vertebral body, spinous process, lamina, facet, other posterior bony structures, or other region of the first vertebra 2a, the anchoring mechanism 40 may be actuated to drive a first anchor 70a into the first vertebra 2a to secure the stabilization member 50 to the first vertebra 2a. For instance, the second handle 34 may be actuated to actuate the driver 46 to push the first anchor 70a from the distal end 16 of the installation tool 10. The first anchor 70a may be driven into the first vertebra 2a through direct translational movement of the first anchor 70a, without rotational movement such as is necessary in installing a pedicle screw. Thus, the first anchor 70a may be installed more quickly than the time necessary to secure a pedicle screw. Note, as discussed above, in some embodiments the first anchor 70a may be driven into the first vertebra 2a by manually delivering and tamping the first anchor 70a into place through a channel along the shaft 14, or otherwise manually driven into the first vertebra 2a.

Figure 4B:
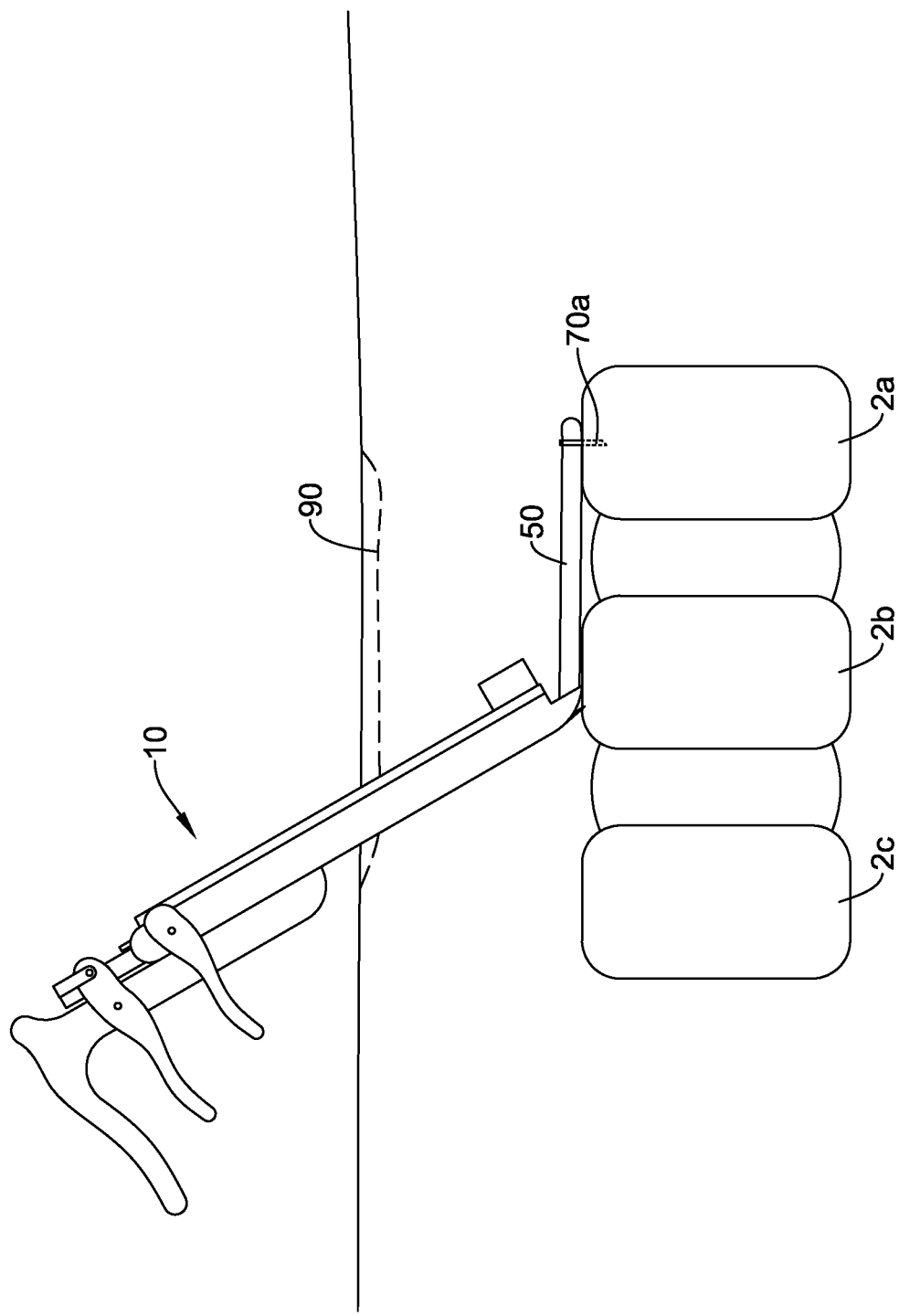

With the stabilization member 50 secured to the first vertebra 2a with the first anchor 70a, the distal end 16 of the installation tool 10 may be moved toward the second vertebra 2b, as shown in FIG. 4B. As the installation tool 10 is moved toward the second vertebra 2b, the stabilization member 50 may be further advanced from the distal end 16 of the installation tool 10, extending the stabilization member 50 from the first vertebra 2a to the second vertebra 2b. For instance, the first handle 32 may be actuated as the distal end 16 of the installation tool 10 is moved to the second vertebra 2b to advance the stabilization member 50 along the conduit 20 and out the distal opening 24 of the installation tool 10.

Positioned adjacent the second vertebra 2b, in some instances the installation tool 10 may be used to distract the second vertebra 2b from the first vertebra 2a to alleviate compression of the spinal column and/or attain a desired spacing between the first vertebra 2a and the second vertebra 2b. For instance, the prong(s) 26 of the installation tool 10 may be engaged with the second vertebra 2b and the installation tool 10 may be manipulated to urge the second vertebra 2b away from the first vertebra 2a. In some instances, a separate distraction tool may be used independently or in conjunction with the installation tool 10 to distract the second vertebra 2b from the first vertebra 2a.

With the installation tool 10 adjacent the second vertebra 2b, the stabilization member 50 may be positioned at a desired location on the second vertebra 2b, such as the pedicle, vertebral body, spinous process, lamina, facet, other posterior bony structures, or other region of the second vertebra 2b. Having completed distraction of the vertebrae 2a, 2b, if any, the anchoring mechanism 40 may then be actuated to drive a second anchor 70b into the second vertebra 2b to secure the stabilization member 50 to the second vertebra 2b, as shown in FIG. 4C. For instance, the second handle 34 may be actuated to actuate the driver 46 to push the second anchor 70b from the distal end 16 of the installation tool 10. The second anchor 70b may be driven into the second vertebra 2b through direct translational movement of the second anchor 70b, without rotational movement such as is necessary in installing a pedicle screw. Thus, the second anchor 70b may be installed more quickly than the time necessary to secure a pedicle screw. Note, as discussed above, in some embodiments the second anchor 70b may be driven into the second vertebra 2b by manually delivering and tamping the second anchor 70b into place through a channel along the shaft 14, or otherwise manually driven into the second vertebra 2b.

Once the stabilization member 50 is secured to the second vertebra 2b with the second anchor 70b, any excess portion of the stabilization member 50 may be cut away from the portion of the stabilization member 50 extending between the first anchor 70a and the second anchor 70b. For instance, as shown in FIG. 4D, the cutter 54 may be actuated to cut away excess portions of the stabilization member 50. This may be achieved, for example, by manipulating the control mechanism 60 such that actuation of the first handle 32 moves the cutter 54 distally allowing the sharpened tip 56 of the cutter 54 to sever the stabilization member 50. As noted above, in other embodiments, the cutter 54 may include jaws which close around the stabilization member 50 through actuation of the first handle 32 to sever the stabilization member 50. In other embodiments, another cutting device may be introduced through the incision 90 to cut away excess portions of the stabilization member 50.

FIG. 4E illustrates the installed vertebral stabilization system 80, including the stabilization member 50 and the first and second anchors 70a, 70b securing the stabilization member 50 to first and second vertebra 2a, 2b, respectively. With the vertebral stabilization system 80 installed, movement between the adjacent vertebrae may be limited to a desired amount and/or increased structural integrity between adjacent vertebrae may be attained. For instance, the stabilization member 50 may provide tensile strength and/or compressive resistance in order to transfer loading of the spinal column. The flexible nature of the stabilization member 50, however, may allow for some dynamic movement of the adjacent vertebrae 2a, 2b relative to each other. Once the vertebral stabilization system 80 has been installed, the installation tool 10 may be removed from the patient's body and the incision 90 closed to complete procedure.

It is noted that in some instances the installation tool 10 may be used to install the stabilization member 50, or another stabilization member 50, across additional vertebrae in a multi-level stabilization system. For instance if it is desired to install the stabilization member across one or more additional vertebrae 2 in a multi-level stabilization system, once the stabilization member 50 has been secured to the second vertebra 2b, the installation tool 10 may be moved toward a third vertebra 2c while advancing the stabilization member 50 from the distal end 16 of the installation tool 10 in a similar manner to that described above. Once the stabilization member 50 is properly placed on the third vertebra 2c, the anchoring mechanism 40 may be actuated to secure the stabilization member 50 to the third vertebra 2c with an anchor 70 in a similar manner to that described above. These steps may be repeated for additional vertebral levels as desired. Any excess portions of the stabilization member 50 may then be cut away, such as with the cutter 54, and then the installation tool 10 may be removed from the patient.

Figure 5:
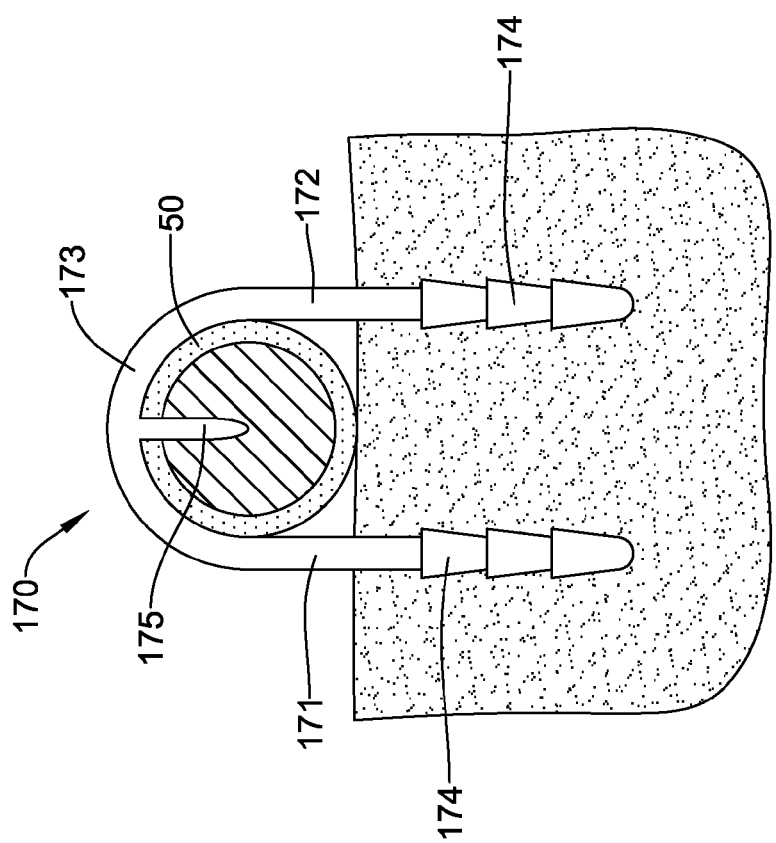
FIGS. 5, 6, 7-7A, 8, 9A-9B and 10A-10B illustrate various exemplary embodiments of an anchor which may be used with the installation tool of FIG. 1.

FIGS. 5, 6, 7-7A, 8, 9A-9B and 10A-10B illustrate some possible configurations of the anchor 70 which may be used with the installation tool 10 to secure a stabilization member 50 to vertebrae of a spinal column. FIG. 5 illustrates a staple 170 which may be used to secure a stabilization member 50 to vertebrae. The staple 170 includes a first leg 171, a second leg 172 and a crown 173 extending between the first leg 171 and the second leg 172. As shown in FIG. 5, in some embodiments the first leg 171 may extend parallel to the second leg 172, while in other embodiments the first leg 171 may be divergent from or convergent to the second leg 172. In some embodiments, the crown 173 may have an arcuate shape curving from the first leg 171 to the second leg 172. Such an arcuate shape may accommodate the shape of a stabilization member 50 such that a convex surface of the stabilization member 50 may rest against or contact a concave surface of the arcuate portion of the crown 173. In other embodiments, the crown 173 may extend linearly between the first leg 171 and the second leg 172 of the staple 170.

The first leg 171 and/or the second leg 172 may include one or more, or a plurality of barbs 174 which may be embedded in the bone of a vertebra to help secure and retain the staple 170 with the vertebra. For instance, the barbs 174 may prevent reverse movement of the legs 171, 172 out of the bone. Furthermore, the crown 173 may include a spike 175 or other projection configured to protrude into and/or penetrate the stabilization member 50. The spike 175 may help prevent movement of the stabilization member 50 relative to the staple 170 when the stabilization member 50 is secured to the vertebra.

When secured to a vertebra, the stabilization member 50 may extend through the central opening of the staple 170 such that the first and second legs 171, 172 of the staple 170 straddle the stabilization member 50 while the stabilization member 50 is positioned between the crown 173 and the vertebra.

Figure 6:
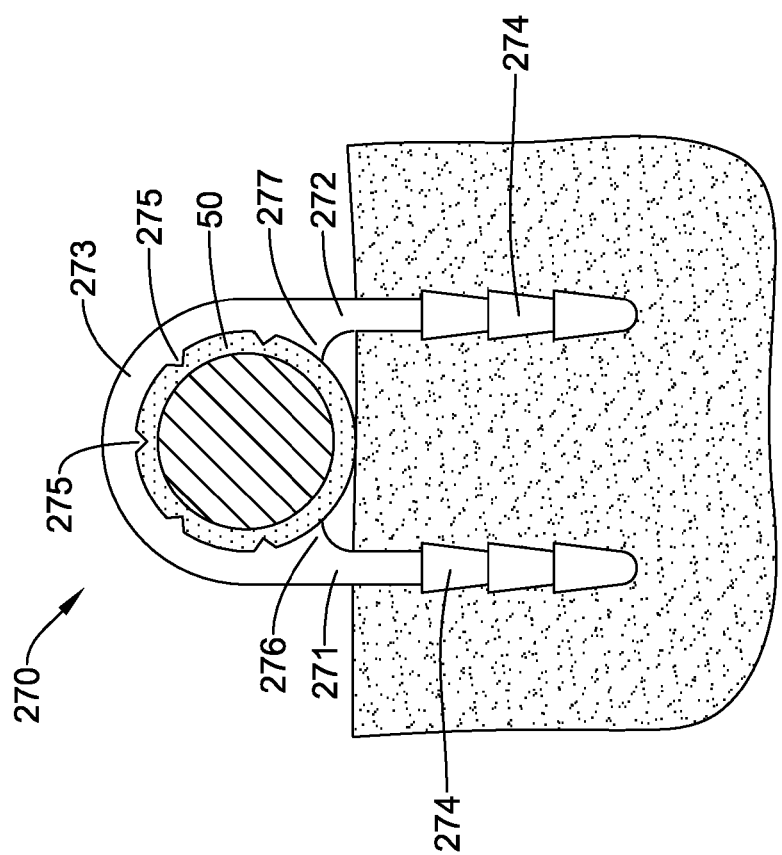

FIG. 6 illustrates another staple 270 which may be used to secure a stabilization member 50 to vertebrae. The staple 270 includes a first leg 271, a second leg 272 and a crown 273 extending between the first leg 271 and the second leg 272. As shown in FIG. 6, in some embodiments the first leg 271 may extend parallel to the second leg 272, while in other embodiments the first leg 271 may be divergent from or convergent to the second leg 272. In some embodiments, the crown 273 may have an arcuate shape curving from the first leg 271 to the second leg 272. Such an arcuate shape may accommodate the shape of a stabilization member 50 such that a convex surface of the stabilization member 50 may rest against or contact a concave surface of the arcuate portion of the crown 273. In other embodiments, the crown 273 may extend linearly between the first leg 271 and the second leg 272 of the staple 270.

The first leg 271 and/or the second leg 272 may include one or more, or a plurality of barbs 274 which may be embedded in the bone of a vertebra to help secure and retain the staple 270 with the vertebra. For instance, the barbs 274 may prevent reverse movement of the legs 271, 272 out of the bone. Furthermore, the crown 273 may include a plurality of projections 275 configured to protrude into and/or penetrate the stabilization member 50. The plurality of projections 275 may extend from the crown 273 along a length of the crown 273 of the staple 270. The plurality of projections 275 may help prevent movement of the stabilization member 50 relative to the staple 270 when the stabilization member 50 is secured to the vertebra.

The staple 270 may also include a first ridge 276 on the first leg 271 and a second ridge 277 on the second leg 272. The first ridge 276 may extend toward the second leg 272 and the second ridge 277 may extend toward the first leg 271. The first and second ridges 276, 277 may be configured such that the ridges 276, 277 are located on an under side of the stabilization member 50 (i.e., between the stabilization member 50 and the vertebra), when the stabilization member 50 is secured to the vertebra with the staple 270.

In some instances, the ridges 276, 277 may help force the stabilization member 50 upward into engagement with the projections 275 protruding from the crown 273 to help retain the stabilization member 50 from moving relative to the staple 270 when secured to a vertebra. In some instances, the stabilization member 50 may be snap fitted into the opening defined between the crown 273 and the first and second ridges 276, 277 to increase the holding ability of the staple 270.

When secured to a vertebra, the stabilization member 50 may extend through the central opening of the staple 270 such that the first and second legs 271, 272 of the staple 270 straddle the stabilization member 50 while the stabilization member 50 is positioned between the crown 273 and the vertebra.

Figure 7A:
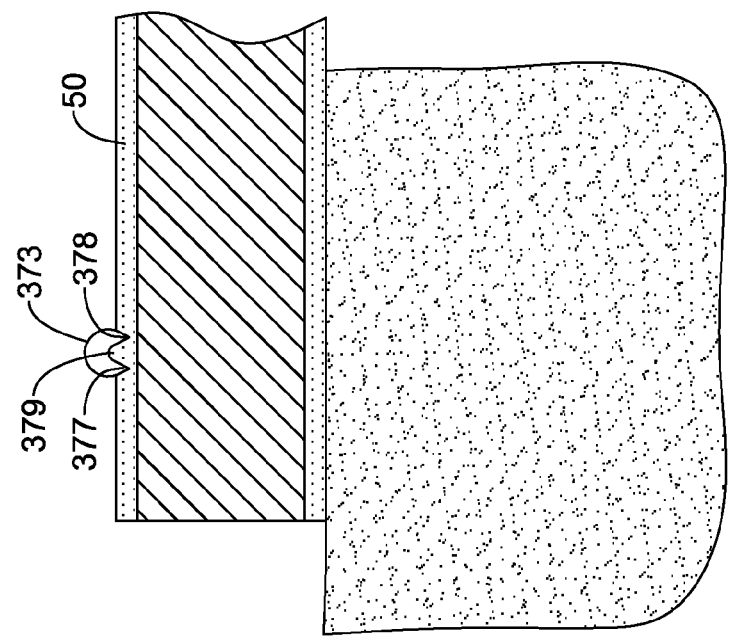
Figure 7:
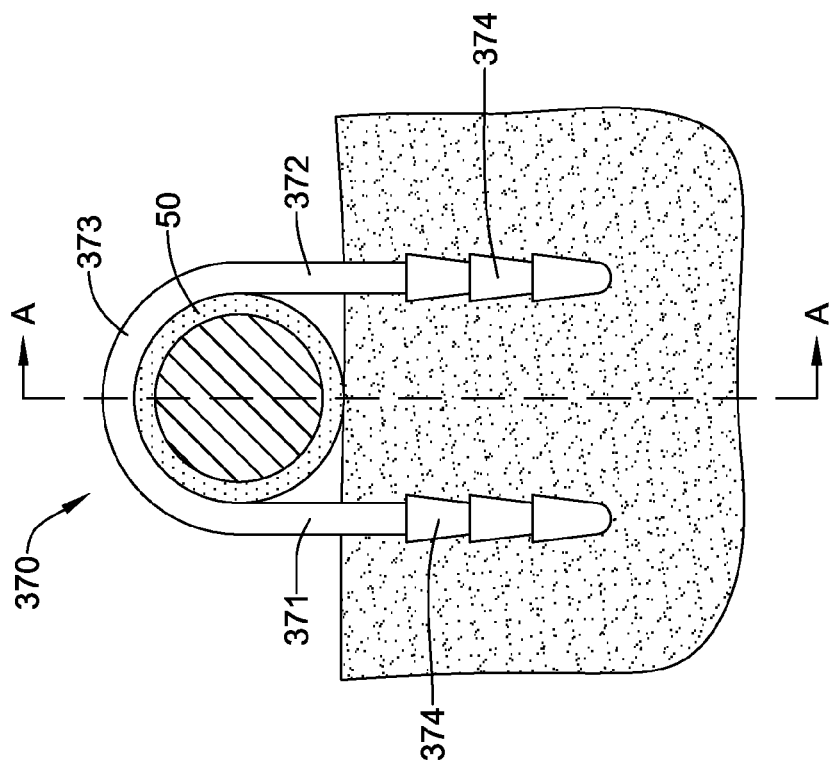

Another embodiment of a staple 370 is illustrated in FIGS. 7 and 7A. The staple 370 includes a first leg 371, a second leg 372 and a crown 373 extending between the first leg 371 and the second leg 372. As shown in FIG. 7, in some embodiments the first leg 371 may extend parallel to the second leg 372, while in other embodiments the first leg 371 may be divergent from or convergent to the second leg 372. In some embodiments, the crown 373 may have an arcuate shape curving from the first leg 371 to the second leg 372. Such an arcuate shape may accommodate the shape of a stabilization member 50 such that a convex surface of the stabilization member 50 may rest against or contact a concave surface of the arcuate portion of the crown 373. In other embodiments, the crown 373 may extend linearly between the first leg 371 and the second leg 372 of the staple 370.

The first leg 371 and/or the second leg 372 may include one or more, or a plurality of barbs 374 which may be embedded in the bone of a vertebra to help secure and retain the staple 370 with the vertebra. For instance, the barbs 374 may prevent reverse movement of the legs 371, 372 out of the bone.

Furthermore, the crown 373 may include a first rib 377 and a second rib 378 extending parallel to the first rib 377 along an inner surface of the crown. The first and second ribs 377, 378 may be arcuate, following the arcuate curvature of the crown 373. In some embodiments, the crown 373 may include a channel 379 between the first rib 377 and the second rib 378. The first and second ribs 377, 378 may engage the stabilization member 50 when the stabilization member 50 is secured to a vertebra with the staple 370 in order to help prevent movement of the stabilization member 50 relative to the staple 270 when the stabilization member 50 is secured to the vertebra.

When secured to a vertebra, the stabilization member 50 may extend through the central opening of the staple 370 such that the first and second legs 371, 372 of the staple 370 straddle the stabilization member 50 while the stabilization member 50 is positioned between the crown 373 and the vertebra.

Figure 8:
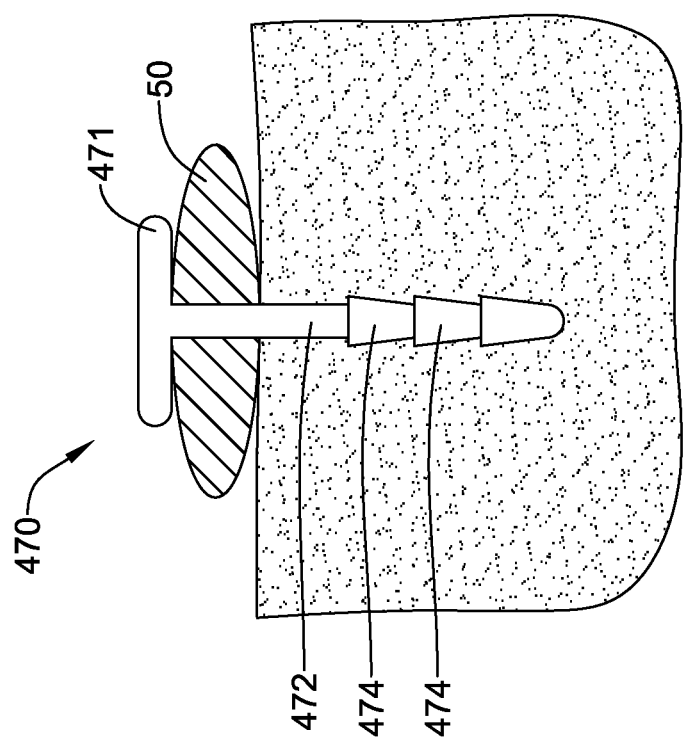

FIG. 8 illustrates a tack 470 which may be used to secure a stabilization member 50 to vertebrae. The tack 470 may include a head 471 and a shaft 472 extending from the head 471. The shaft 472 may include one or more, or a plurality of barbs 474 which may be embedded in the bone of a vertebra to help secure and retain the tack 470 with the vertebra. For instance, the barbs 474 may prevent reverse movement of the tack 470 out of the bone.

When secured to a vertebra, the tack 470 may pierce the stabilization member 50 such that the head 471 presses against the stabilization member 50 while the shaft 472 extends through the stabilization member 50 and into the vertebra. In other embodiments, the stabilization member 50 may include a hole through which the shaft 472 of the tack 470 extends through.

Figure 9A:
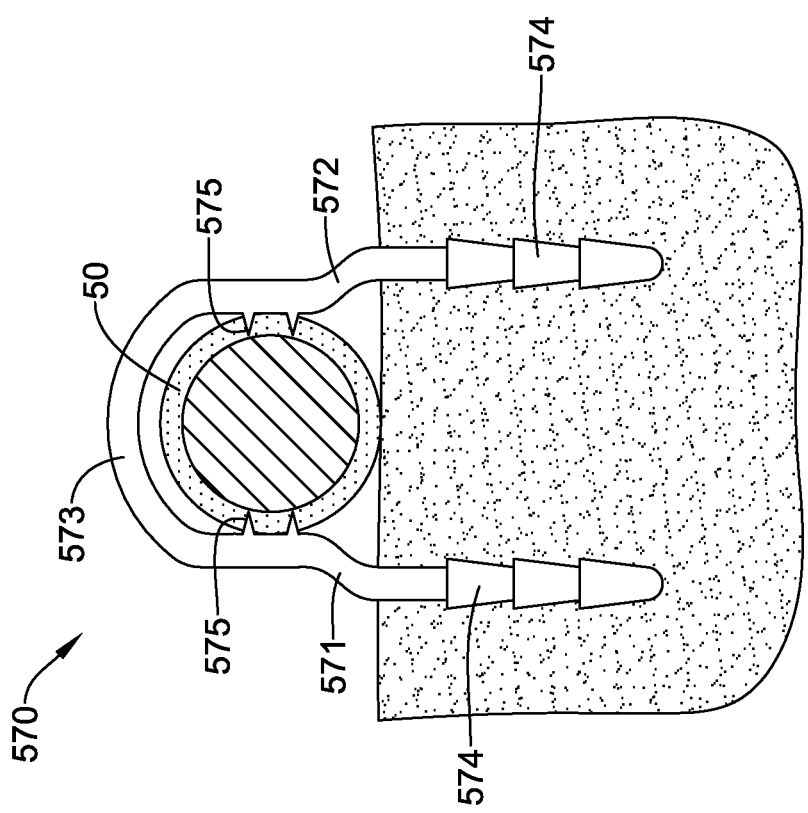
Figure 9B:
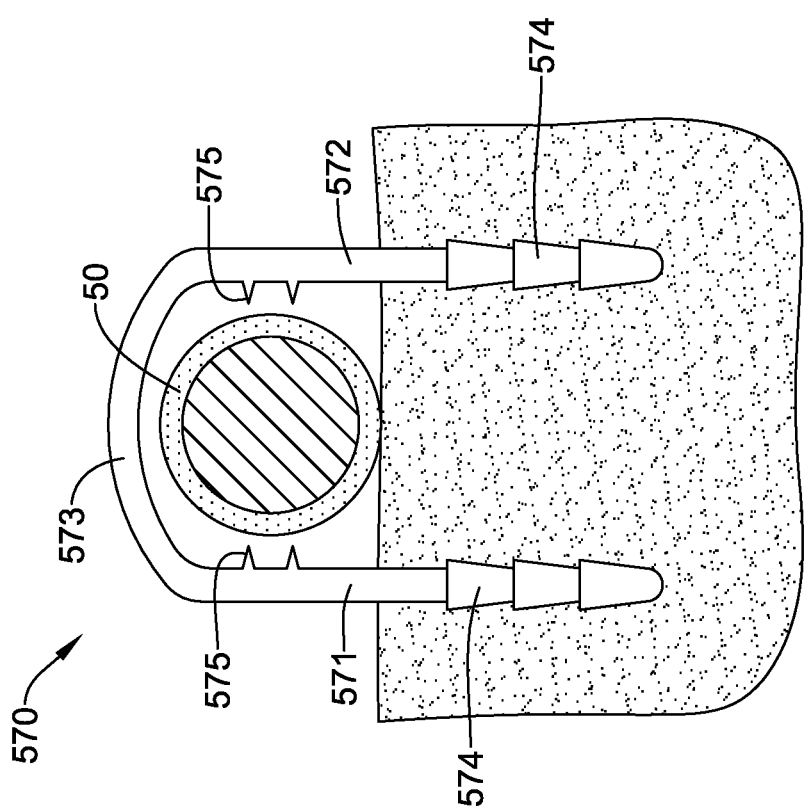

Another staple 570 which may be used to secure a stabilization member 50 to vertebrae is shown in FIGS. 9A-9B. The staple 570 includes a first leg 571, a second leg 572 and a crown 573 extending between the first leg 571 and the second leg 572. As shown in FIG. 9A, initially the first leg 571 may extend parallel to the second leg 572. Furthermore, the crown 573 may have an arcuate shape curving from the first leg 571 to the second leg 572. Such an arcuate shape may accommodate the shape of a stabilization member 50 such that a convex surface of the stabilization member 50 may rest against or contact a concave surface of the arcuate portion of the crown 573. In other embodiments, the crown 573 may extend linearly between the first leg 571 and the second leg 572 of the staple 570.

The first leg 571 and/or the second leg 572 may include one or more, or a plurality of barbs 574 which may be embedded in the bone of a vertebra to help secure and retain the staple 570 with the vertebra. For instance, the barbs 574 may prevent reverse movement of the legs 571, 572 out of the bone. Furthermore, the crown 573 may include a plurality of projections 575 configured to protrude into and/or penetrate the stabilization member 50. The plurality of projections 575 may extend lateral toward one another between the first leg 571 and the second leg 572. The plurality of projections 575 may help prevent movement of the stabilization member 50 relative to the staple 570 when the stabilization member 50 is secured to the vertebra.

When secured to a vertebra, the stabilization member 50 may extend through the central opening of the staple 570 such that the first and second legs 571, 572 of the staple 570 straddle the stabilization member 50 while the stabilization member 50 is positioned between the crown 573 and the vertebra. As shown in FIG. 9B, with the stabilization member 50 positioned between the first and second legs 571, 572, the legs 571, 572 may be laterally crimped toward one another to secure the stabilization member 50 between the legs 571, 572. Crimping of the legs 571, 572 may force the projections 575 into engagement with the stabilization member 50 such that the projections 575 project into and/or penetrate the stabilization member 50. Crimping the staple 570 may help prevent movement of the stabilization member 50 relative to the staple 570 when the stabilization member 50 is secured to the vertebra.

Figures 10A, 10B:
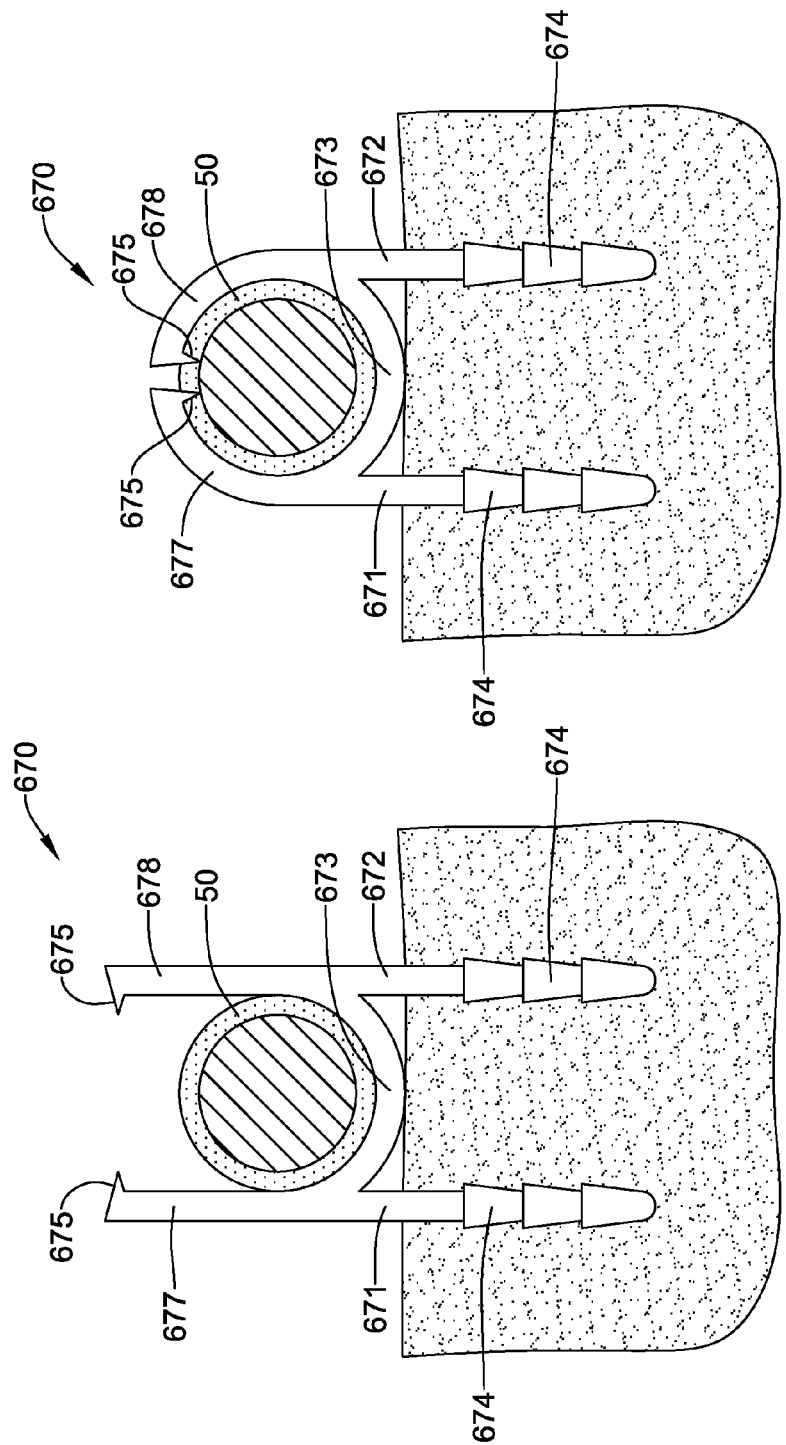

Yet another staple 670 which may be used to secure a stabilization member 50 to vertebrae is shown in FIGS. 10A-10B. The staple 670 includes a first leg 671, a second leg 672 and a cross member 673 extending between the first leg 671 and the second leg 672. As shown in FIG. 10A, in some embodiments the first leg 671 may extend parallel to the second leg 672, while in other embodiments the first leg 671 may be divergent from or convergent to the second leg 672.

The staple 670 may also include a first arm 677 and a second arm 678 extending from the cross member 673 in a direction generally opposite that of the first and second legs 671, 672. In embodiments, the first and second arms 677, 678 may be extensions of the first and second legs 671, 672, respectively, extending in opposing directions from the cross member 673.

As shown in FIG. 10A, initially the staple 670 may have a generally H-shape in which the first leg 671 extends parallel to the second leg 672, and the first arm 677 extends parallel to the second arm 678. The cross member 673 may have an arcuate shape curving from the first leg 671 and first arm 677 to the second leg 672 and second arm 678. Such an arcuate shape may accommodate the shape of a stabilization member 50 such that a convex surface of the stabilization member 50 may rest against or contact a concave surface of the arcuate portion of the cross member 673. In other embodiments, the cross member 673 may extend linearly from the first leg 671 and first arm 677 to the second leg 672 and second arm 678 of the staple 670.

The first leg 671 and/or the second leg 672 may include one or more, or a plurality of barbs 674 which may be embedded in the bone of a vertebra to help secure and retain the staple 670 with the vertebra. For instance, the barbs 674 may prevent reverse movement of the legs 671, 672 out of the bone. Furthermore, the first arm 677 and/or the second arm 678 may include one or more, or a plurality of projections 675 configured to protrude into and/or penetrate the stabilization member 50. The projections 675 may extend lateral toward one another between the first arm 677 and the second arm 678. The projections 675 may help prevent movement of the stabilization member 50 relative to the staple 670 when the stabilization member 50 is secured to the vertebra.

When secured to a vertebra, the stabilization member 50 may extend through the central opening of the staple 670 between the first and second arms 677, 678 such that the first and second arms 677, 678 of the staple 670 straddle the stabilization member 50. Furthermore, the cross member 673 may be located between the stabilization member 50 and the vertebra. As shown in FIG. 10B, with the stabilization member 50 positioned between the first and second arms 677, 678, the arms 677, 678 may be crimped around a portion of the stabilization member 50 to secure the stabilization member 50 between the arms 677, 678 and the cross member 673. Thus, the arms 677, 678 may be crimped into an arcuate shape around a portion of the perimeter of the stabilization member 50. Crimping of the first and second arms 677, 678 may force the projections 675 into engagement with the stabilization member 50 such that the projections 675 project into and/or penetrate the stabilization member 50. Crimping the staple 670 may help prevent movement of the stabilization member 50 relative to the staple 670 when the stabilization member 50 is secured to the vertebra.

FIGS. 11A-11D illustrate some possible configurations of the stabilization member 50 which may provide tensile strength and compressive resistance. The stabilization member 150 may include an outer layer 152 surrounding an inner core layer 154. The outer layer 152 may provide tensile strength while the inner core layer 154 may provide compressive resistance to the stabilization member 150. For instance, the outer layer 152 may be a knit, braided or woven jacket of material overlaying the inner core layer 154 which may be placed in tension. The inner core layer 154 may be formed of a solid material, such as a solid polymeric material (e.g., an elastomer), which may be placed in compression.

FIG. 11B illustrates another stabilization member 250 which may be subjected to tensile and compressive loading. The stabilization member 250 may include an inner core layer 256, an intermediate layer 254 surrounding the inner core layer 256, and an outer layer 252 surrounding the intermediate layer 254. As shown in FIG. 11B, the inner core layer 256 may include one or more filaments or strands intermingled (e.g., twisted, woven, braided, knitted) together. The intermediate layer 254 may be formed of a solid material, such as a solid polymeric material (e.g., an elastomer), placed or formed over the inner core layer 256. The outer layer 252 may be a knit, braided or woven jacket of material overlaying the intermediate layer 254. The inner core layer 256 and/or the outer layer 252 may transfer tensile loads through the stabilization member 250 and the intermediate layer 254 may transfer compressive loads through the stabilization member 250.

FIG. 11C illustrates another stabilization member 350 which may be subjected to tensile and compressive loading. The stabilization member 350 may include an outer layer 352 surrounding an inner core layer 354. The outer layer 352 may provide tensile strength while the inner core layer 354 may provide compressive resistance to the stabilization member 350. For instance, the outer layer 352 may be a knit, braided or woven jacket of material overlaying the inner core layer 354 which may be placed in tension. The inner core layer 354 may be formed of a solid material, such as a solid polymeric material (e.g., an elastomer), which may be placed in compression. As shown in FIG. 11C, the inner core layer 354 may have an oval, or flattened cross section, which may allow for a larger surface area of the stabilization member 350 to be in contact with the vertebrae of the spinal column, without deformation of the stabilization member 350. The outer layer 352 may transfer tensile loads through the stabilization member 350 and the inner core layer 354 may transfer compressive loads through the stabilization member 350.

FIG. 11D illustrates yet another stabilization member 450 which may be subjected to tensile and compressive loading. The stabilization member 450 may include a first core layer 454 and a second core layer 456 extending axially through an outer layer 452. The first core layer 454 may be spaced from the second core layer 456 and extending parallel to the second core layer 456 along the length of the stabilization member 450. Each of the first core layer 454 and the second core layer 456 may include one or more filaments or strands intermingled (e.g., twisted, woven, braided, knitted) together. The outer layer 452 may be formed of a solid material, such as a solid polymeric material (e.g., an elastomer), placed or formed over the first and second inner core layers 454, 456. As shown in FIG. 11D, the outer layer 452 may have an oval, or flattened cross section, which may allow for a larger surface area of the stabilization member 450 to be in contact with the vertebrae of the spinal column, without deformation of the stabilization member 450. Furthermore, in some instances, an anchor may penetrate the central portion of the outer layer 452 between the first and second inner core layers 454, 456 to secure the stabilization member 450 to a vertebra. The first and second inner core layers 454, 456 may transfer tensile loads through the stabilization member 450 and the outer layer 452 may transfer compressive loads through the stabilization member 450.

In some embodiments, the stabilization member 50 may be a monolithic structure formed of a single piece of flexible material, including natural or synthetic elastomers, thermoplastic elastomers, for example, polyurethane elastomers such as polycarbonate urethane, or other polymeric materials. The stabilization member 50 may be molded, extruded, or otherwise formed from a desired material. In such an embodiment, the stabilization member 50 may be able to withstand both tensile and compressive loads, as desired.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method installing a vertebral stabilization system, the method comprising:

positioning a first anchor and a second anchor in a cartridge of an anchoring mechanism proximate a distal end of an installation tool;

inserting the installation tool through an incision toward a vertebral body of a first vertebra such that the distal end of the installation tool is positioned proximate the vertebral body of the first vertebra;

using the installation tool, securing the first anchor into the vertebral body of the first vertebra to secure a flexible implant member to the vertebral body of the first vertebra;

moving the distal end of the installation tool to a position proximate a vertebral body of a second vertebra without removing the installation tool from the incision;

manipulating the installation tool to apply a desired amount of tension on the flexible implant member, and using the installation tool, securing the second anchor into the vertebral body of the second vertebra to secure the flexible implant member to the vertebral body of the second vertebra.

2. The method of claim 1, wherein the desired amount of tension is applied on the flexible implant member by distracting the second vertebra from the first vertebra.

3. The method of claim 1, wherein manipulating the installation tool includes attaining a desired spacing between the first vertebra and the second vertebra.

4. The method of claim 1, wherein the flexible implant member is maintained in tension after securing the first and second anchors to the vertebral bodies of the first and second vertebrae, respectively.

5. The method of claim 1, wherein the flexible implant member is inserted through the incision through a conduit of the installation tool.

6. The method of claim 5, wherein the flexible implant member is positioned in the conduit prior to inserting the installation tool through the incision.

7. The method of claim 5, further comprising:
advancing a portion of the flexible implant member out of the conduit while moving the distal end of the installation tool to the position proximate the vertebral body of the second vertebra.

8. The method of claim 1, wherein the anchoring mechanism which is actuatable to secure the first and second anchors to the vertebral bodies of the first and second vertebrae, respectively.

9. The method of claim 1, further comprising:
cutting away an excess portion of the flexible implant member after securing the flexible implant member to the vertebral bodies of the first and second vertebrae.

10. The method of claim 9, further comprising:
withdrawing the excess portion of the flexible implant member while withdrawing the installation tool from the incision.

11. The method of claim 1, wherein during the manipulating the installation tool step a portion of the installation tool is engaged with the vertebral body of the second vertebra.

12. The method of claim 11, wherein the portion of the installation tool engaged with the vertebral body of the second vertebra is a prong.

13. The method of claim 12, wherein the prong extends from the distal end of the installation tool.

14. The method of claim 1, wherein the installation tool is inserted through the incision via a lateral approach.

15. The method of claim 1, further comprising:
actuating a first handle of the installation tool to advance a portion of the flexible implant member out of the installation tool.

16. The method of claim 15, further comprising:
actuating a second handle of the installation tool to secure the first anchor into the vertebral body of the first vertebra.

17. The method of claim 16, further comprising:
actuating the second handle of the installation tool to secure the second anchor into the vertebral body of the second vertebra.

18. The method of claim 1, wherein the installation tool includes a ramp to redirect the flexible implant member from the installation tool.

19. A method of installing a vertebral stabilization system, the method comprising:
inserting an installation tool through an incision toward a vertebral body of a first vertebra such that a distal end of the installation tool is positioned proximate the vertebral body of the first vertebra;
using the installation tool, securing a first staple into the vertebral body of the first vertebra to secure a flexible implant member to the vertebral body of the first vertebra;
moving the distal end of the installation tool to a position proximate a vertebral body of a second vertebra without removing the installation tool from the incision;
manipulating the installation tool to apply a desired amount of tension on the flexible implant member, and
using the installation tool, securing a second staple into the vertebral body of the second vertebra to secure the flexible implant member to the vertebral body of the second vertebra.

20. The method of claim 19, wherein manipulating the installation tool includes attaining a desired spacing between the first vertebra and the second vertebra.

* * * * *